United States Patent [19]

Lehmann et al.

[11] 4,062,732

[45] Dec. 13, 1977

[54] PROCESS OF PRODUCING ACID STABLE PROTEASE

[75] Inventors: Rudolf Lehmann, Neuss; Hans F. Pfeiffer, Haan; Joachim Schindler, Dusseldorf-Benrath; Wolfgang Schreiber, Langenfeld, all of Germany

[73] Assignee: Henkel Kommanditgesellschaft auf Aktien, Dusseldorf-Holthausen, Germany

[21] Appl. No.: 695,453

[22] Filed: June 14, 1976

[30] Foreign Application Priority Data

June 26, 1975 Germany ............................. 2528490

[51] Int. Cl.² .................................................... C12D 13/10
[52] U.S. Cl. .................................. 195/66 R; 195/62; 195/65; 426/53
[58] Field of Search ....................... 195/62, 65, 66 R; 426/63, 53

[56] References Cited

U.S. PATENT DOCUMENTS

| 3,674,644 | 7/1972 | Yokotsuka et al. | 195/62 |
| 3,677,898 | 7/1972 | Mitsugi et al. | 195/62 |
| 3,694,316 | 9/1972 | Kawai et al. | 195/66 R |

*Primary Examiner*—Lionel M. Shapiro
*Attorney, Agent, or Firm*—Hammond & Littell

[57] ABSTRACT

An acid stable protease whose pH range of 50% of maximum activity is between pH 2.5 and 6.5, produced by culturing a fungus strain of the species *Rhizopus rhizopodiformis* CBS 227.75 under aerobic conditions in a nutrient medium containing assimilable carbon and nitrogen sources, at a pH between 3 and 7 and at a temperature between 25° C and 50° C, and separating the enzyme produced; as well as the method of production, its use as a foodstuff additive and foodstuffs containing the same.

1 Claim, No Drawings

PROCESS OF PRODUCING ACID STABLE PROTEASE

RELATED ART

It is generally known and the subject of many industrial production methods to obtain proteolytic enzymes with an acid pH activity range from the growth in nutrient media of microorganism of various species, e.g. strains of the species Alternaria, Aspergillus, Fusarium, Paecilomyces, Pencillium, Rhizopus and Trametes. These proteases have an optimum effect at a specific pH, generally called the "pH-optimum", but their activity drops rapidly at either side of this optimum pH value. A meaningful application or use of these proteases requires, therefore, the knowledge of the effective pH value for application of the protease, which is not always given or known. Besides, it is necessary to select each time a suitable protease for use at a given pH value.

OBJECTS OF THE INVENTION

An object of the invention is, therefore, to find an acid stable protease with good activity over a wide pH range and high enzymatic activity.

Another object of the invention is the obtaining of an acid stable protease whose pH range of 50% of maximum activity is between a pH of 2.5 and a pH of 6.5, which is produced by culturing a fungus strain of the species Rhizopus rhizopodiformis CBS 227.75 under aerobic conditions in a nutrient medium containing assimilable carbon and nitrogen sources, at a pH of between 3 and 7 and at a temperature of between 25° C and 50° C, separating the mycelium, and recovering said protease.

A further object of the invention is the development of a process for the production of an acid stable protease whose pH range of 50% of maximum activity is between a pH of 2.5 and a pH of 6.5, consisting essentially of culturing a fungus strain of the species Rhizopus rhizopodiformis CBS 227.75 under aerobic conditions in a nutrient medium containing assimilable carbon and nitrogen sources, at a pH of beween 3 and 7 and at a temperature of between 25° C and 50° C, separating the mycelium, and recovering said protease.

A yet further object of the present invention is the development of a feedstuff additive and a feedstuff containing an effective amount of the above acid stable protease.

These and other objects of the present invention will become more apparent as the description thereof proceeds.

DESCRIPTION OF THE INVENTION

The obtention of an acid stable protease whose pH range of 50% of maximum activity is between a pH of 2.5 and a pH of 6.5 is of particular importance when the said protease is to be used in the food and animal feed industry.

The subject of the present invention is a method for the preparation of an acid stable protease with a wide pH activity range by growing a fungus strain of the species Rhizopus rhizopodiformis under aerobic conditions in a nutrient medium which contains assimilable carbon and nitrogen sources, at pH values of between 3 and 7, and at temperatures between 25° C and 50° and by and separating the enzyme produced. More particularly, the present invention relates to an acid stable protease whose pH range of 50% of maximum activity is between a pH of 2.5 and a pH of 6.5, which is produced by culturing a fungus strain of the species Rhizopus rhizopodiformis CBS 227.75 under aerobic conditions in a nutrient medium containing assimilable carbon and nitrogen sources, at a pH of between 3 and 7 and at a temperature of between 25° C and 50° C, separating the mycelium, and recovering said protease; as well as a process for the production of an acid stable protease whose pH range of 50% of maximum activity is between a pH of 2.5 and a pH of 6.5, consisting essentially of culturing a fungus strain of the species Rhizopus rhizopodiformis CBS 227.75 under aerobic conditions in a nutrient medium containing assimilable carbon and nitrogen sources, at a pH of between 3 and 7 and at a temperature of between 25° C and 50° C, separating the mycelium, and recovering said protease.

The species Rhizopus rhizopodiformis utilized in the present invention was deposited at the Central Bureau voor Schimmelcultures, Baarn, the Netherlands, on Mar. 23, 1975 under the Deposit No. CBS 227.75, subject to access by the public on grant of a patent.

The species Rhizopus rhizopodiformis was isolated under specific enrichment conditions at pH values of between 3 and 5 from earth samples by culturing with proteins, like casein and gelatin as carbon and nitrogen sources. It was classified at the Central Bureau voor Schimmelcultures, Baarn, the Netherlands, as *Rhizopus rhizopodiformis*(Cohn) Zopf (=R. cohnii Berlese & de Toni), who stated that this relatively minor species still grows at 50° C.

The method for the preparation of the protease can be carried out in a liquid or solid nutrient medium, but a liquid medium is generally preferred. The growing in a nutrient medium is effected according to the conventional shaking culture or fermentation method.

The nutrient medium to be used according to the invention is prepared in known manner, and should contain a carbon source, a nitrogen source, and other nutrients and growth substances required by the microorganism. Suitable carbon sources are starches, dextrin, cane sugar, glucose, fructose, maltose and sugar-containing wastes. Suitable nitrogen sources are ammonium salts, urea, casein, gelatin, corn steepwater and soybean flour or soybean cake. Futhermore, inorganic salts, such as sodium hydrogen phosphates, potassium hydrogen phosphates, ammonium hydrogen phosphates, calcium and magnesium salts, can be added to the nutrient medium. Furthermore, it may be of advantage to add growth promoting substances to the nutrient medium, such as yeast extracts and vitamins.

The fermentation temperature can vary between 25° C and 50° C, but is preferably maintained between 27° C and 32° C. The pH value of the nutrient medium can vary between 3.0 and 7.0, and is preferably maintained between a pH of 4.0 and a pH of 6.0. The growth is effected generally within a period of 20 to 96 hours.

The protease obtained according to the method of the invention can be concentrated and precipitated from the filtered or centrifuged nutrient solution according to conventional methods, first by separating the mycelium and then by adding organic solvents or by salting out with sodium chloride, sodium sulfate, ammonium sulfate or calcium chloride. It can be purified by dialysis or by treatment with ion exchange resins.

The protease produced according to the invention has a particularly wide activity spectrum in the weakly acid region between a pH of 2.5 and a pH of 6.5. The optimum activity is at a pH of 4.5, the range of the 80% maximum activity is from a pH of 3.3 to a pH of 5.9. The range of the 60% maximum activity is from a pH of 3.0 to a pH of 6.4, and the range of 50% of maximum activity is between a pH of 2.5 and a pH of 6.5. The protease is particularly suitable as an additive for animal feeds, especially to improve the results of growing and fattening fowl, pigs, calves and commercially raised fish. It is customarily employed in amounts of from 20 ppm to 2000 ppm of the animal feed. Beyond that it can also be used for other purposes where acid stable proteases are used, such as in the food processing industry, in hospitals and in the household, as an aid in tanning leather, also in a highly-purified form as a digestive in medical applications.

The proteolytic activity of the acid stable protease of the invention was determined according to the known principle of the determination according to Anson. A properly diluted amount of enzyme solution was incubated at 40° C for 20 minutes with an equal volume of a 1.2% casein solution, which contained 0.6% lactic acid, 6M of urea, and 0.1M of citric or acetic acid. The pH value of the casein solution was adjusted to 4.5 by ading 2N sodium hydroxide solution. After the incubation, 0.4N trichloroacetic acid solution was added in a ratio of 1:1. The precipitate formed was filtered off from the undigested casein and the protein fragments in the filtrate formed during the decomposition were determined according to any known protein determination method. Particularly suitable is the method described by Layne in "Methods of Enzymology", Vol. 3, (1957), p. 448 ff.

For each determination a blank value must also be determined by adding first trichloroacetic acid and then casein solution. This blank value indicates, in addition to the blank value of the reagents, also the portion of low-molecular-weight peptides which was already present in the enzyme solution before the digestion. The difference between principle and blank values is compared in the indicated method with the extinction which a known amount of tyrosine supplies in this determination. This amount of tyrosine is then a measure for the proteolytic activity of the enzyme in question. An enzyme unit (TU) is the amount of enzyme which causes the same extinction difference between the principle and blank values per minute as 1M tyrosine solution which is used instead of the enzyme solution.

The measurement of the proteolytic activity at higher and lower pH values than 4.5 is readily possible by suitable standardization of the casein solution, but in this case the acetic acid is preferably replaced by citric acid.

The following examples are illustrative of the practice of the invention without being limitative in any respect.

EXAMPLE 1

For the preparation of the nutrient medium, 3 gm of soybean flour, 3 gm of corn steepwater, 15 gm of casein, 7 gm of gelatin, 2.4 gm of $KH_2PO_4$, 0.5 gm of $MgSO_4 \cdot 7H_2O$, 0.1 gm of $MnCl_2 \cdot 4H_2O$, 0.1 gm of $CaCl_2 \cdot 2H_2O$ and 20 gm of corn starch were dissolved or dispersed in 1 liter of water. The pH value of the nutrient solution was 5.3. The cornstarch was decomposed to a great extent by amylase and the solution was sterilized. Spores of the strain Rhizopus rhizopodiformis CBS 227.75 were inolculated into the sterilized solution and the culture was grown under optimum aeration at 30° C for about 50 hours. After this period, the mycelium was filtered off and the mycelium-free culture broth was used for the determination of the protease activity according to the above-described method. It was found that the culture solution attained an enzymatic activity of up to 18 mTU/ml.

EXAMPLE 2

For the preparation of the nutrient medium, 10 gm of soybean flour (oil-free), 5 gm of corn steepwater, 12 gm of casein, 5 gm of gelatin, 5 gm of dried distillers grains, 2.4 gm of $KH_2PO_4$. 1 gm of $NaNO_3$, 1 gm of $NH_4Cl$, 0.01 gm of $FeSO_4$ and 30 gm of native cornstarch were dissolved or dispersed in 1 liter of tap water. The pH value of the nutrient solution was adjusted to 5.3 after autoclaving. A ten liter fermenter was charged with this nutrient solution, to which was added 100 ml of Czapek-Dox preculture (with 5% starch and 0.5% yeast extract). The nutrient medium was inoculated with spores of the strain Rhizopus rhizopodiformis CBS 227.75 and shaken for 24 hours at 30° C and aerated at 30° C for about 50 hours, until the pH value had risen to 6.8 to 7.0. Then the mycelium was filtered off and the clear culture broth was used for the determination of the protease activity according to the above-described method. It was found that the culture solution attained an enzymatic activity of up to 20 mTU/ml.

The protease was isolated by clear filtration of the broth, after adding 5 gm of Filter Cel and 5 gm of standard Super Cel (Johns-Mansville), concentration at 50 Torr to a third of the original volume, and precipitation by adding 39% of anhydrous sodium sulfate with stirring, while bringing the temperature to 38° to 40° C. Alternately, the protease can also be precipitated from the clear filtered broth by adding thereto 2 volumes of ethanol, methanol, acetone or other water-miscible solvents dropwise at a temperature of −3° to 5° C. The precipitate was vacuum filtered and dried under vacuum.

EXAMPLE 3

Using the above-described method of protease determination, the activity of the protease isolated according to Examples 1 and 2 was determined in dependence on the pH value. The following table contains the pH values for the optimum activity and for 50% of the maximum activity measured at the optimum pH value of various commercially available protease preparations as well as that of the invention. As it can be seen from the values for acid proteases known in the literature, which are likewise listed in this table, the protease of the invention has a wide and, for the above-mentioned applications, more favorable range of activity, expressed in pH units, than the known enzymes.

TABLE

| Enzyme | Optimum pH | pH Range for 50% of Maximum Activity |
|---|---|---|
| Takamine ® Acid fungal protease | 2.5–3.0 | 1.5–4.0 |
| Denapsin ® Aspergillus acid protease | 3.0 d 2.5 | 1.5–4.5 1.5–4.0 |
| Proctase ® | 2.0–3.0 | 1.5–4.5 |
| Samprose ® | 2.5 | 2.0–4.5 |
| Protease from Rhizopus rhizopodiformis CBS 227.75 | 4.0–4.5 | 2.5–6.5 |

EXAMPLE 4

ANIMAL FEED

One ton of a conventional calves starter and weaning feed was employed and mixed with 200 ppm of the solid protease isolated by the process of Example 2.

EXAMPLE 5

ANIMAL FEED ADDITIVE

A conventional mineral and vitamin supplement was prepared containing a balanced amount of minerals and vitamins for fortifying an animal feed at the level of 2.5%. This supplement was sprayed with 10% by weight of the solution of protease obtained by Example 1, having an enzymatic activity of 18 m/TU/ml at a pH of 4.5.

The preceding specific embodiments are illustrative of the practice of the invention. It is to be understood, however, that other expedients known to those skilled in the art or disclosed herein may be employed without departing from the spirit of the invention or the scope of the appended claims.

We claim:

1. A process for the production of an acid stable protease whose pH range of 50% of maximum activity against casein is between a pH of 2.5 and a pH of 6.5, consisting essentially of culturing a fungus strain of the species Rhizopus rhizopodiformis CBS 227.75 under aerobic conditions in a nutrient medium containing assimilable carbon and nitrogen sources, at a pH of between 3 and 7 and at a temperature of between 25° C and 50° C, separating the mycelium, and recovering said protease.

* * * * *